United States Patent
De La Mora et al.

[11] Patent Number: 5,936,242
[45] Date of Patent: Aug. 10, 1999

[54] METHOD AND APPARATUS FOR SEPARATION OF IONS IN A GAS FOR MASS SPECTROMETRY

[75] Inventors: Juan Fernandez De La Mora, New Haven, Conn.; Luis De Juan, Marseilles, France; Thilo Eichler, Stockelsdorf, Germany; Joan Rosell, Castro Valley, Calif.

[73] Assignee: Yale University, New Haven, Conn.

[21] Appl. No.: 09/138,981

[22] Filed: Aug. 24, 1998

Related U.S. Application Data

[62] Division of application No. 08/881,060, Jun. 24, 1997, Pat. No. 5,869,831
[60] Provisional application No. 60/020,697, Jun. 27, 1996.
[51] Int. Cl.⁶ .................................. H01J 49/26
[52] U.S. Cl. ............................................. 250/288
[58] Field of Search .................. 250/288, 282, 250/281

[56] References Cited

U.S. PATENT DOCUMENTS 5,631,462  5/1997  Reents, Jr. ............................. 250/288

Primary Examiner—Kiet T. Nguyen

[57] ABSTRACT

An analytical apparatus provides for the separation and analysis of a subset of ions from a mixture of ions in a gas. The apparatus includes an ion supply, such as an electrospray, which provides a population of variously charged ions. An analyzing chamber is coupled to the ion supply and includes a first wall with an inlet orifice for receiving the flow of variously charged ions, and a second wall opposed to the first wall. A laminar gas flow is established within the analyzing chamber along a flow axis. The second wall is provided with an outlet orifice that is displaced by a determined distance along the gas flow axis from the inlet orifice. A potential difference is applied between the first and second walls which causes the flow of ions, introduced via the inlet orifice, to migrate towards the outlet orifice. The laminar gas flow displaces ion flight trajectories along the flow axis, so that only the ions with a mobility near a specific value reach the second wall close enough to the outlet orifice to be sampled through it. The outlet orifice is coupled to the inlet of a mass spectrometer to enable analysis of the ions emerging from the outlet orifice.

3 Claims, 3 Drawing Sheets

METHOD AND APPARATUS FOR SEPARATION OF IONS IN A GAS FOR MASS SPECTROMETRY

This application is a Division of 08/881,060 filed Jun. 24, 1997, now U.S. Pat. No. 5,869,831.

This Application claims priority from Provisional patent application Ser. No. 60/020,697, filed Jun. 27, 1996.

The United States Government has rights in this invention as a result of support of the development thereof by National Science Foundation Grants CTS 9106619 and CTS-9419051.

FIELD OF THE INVENTION

This invention relates to a method and apparatus for the separation and identification of ions in complex ion mixtures and, more particularly, to a method and apparatus for analysis of various ions through use of a differential mobility analyzer.

BACKGROUND OF THE INVENTION

A variety of techniques are presently in use to enable chemical analysis of ions in ion mixtures. Many such techniques rely on introducing in a gaseous atmosphere, ions from a substance originally dissolved in a liquid, and then analyzing such ions in a mass spectrometer. Sometimes, however, a large number of different species produced by the ionization process give rise to too complex a mass spectrum for individual mass peaks to be recognizable. This circumstance is particularly common for ion sources such as electrosprays, which yield each species in a multitude of charge states, especially in the case of analytes with very large molecular weights.

An electrospray atomizer is implemented by feeding an electrically conductive liquid through a tube, while a liquid meniscus emerging out of the tube is maintained at several kilovolts relative to a reference electrode positioned a few tube diameters away. This liquid meniscus assumes a conical shape under the action of the applied electric field, with a thin jet of solvent/solute emerging from the cone tip. This jet breaks up farther down stream into a spray of fine, charged droplets.

A distinct advantage which arises from the electrospray apparatus is that the generated droplets exhibit a net charge on their respective surfaces. This charge enables the particles to be guided and collected for a variety of purposes. Further, charge repulsion among the droplets prevents an agglomeration thereof. As liquid in the charged droplets evaporates, the electric charge may cause the droplets to further subdivide, which eventually creates arbitrarily small droplets, residue particles and even ions. Many of such particles hold enough charge not to be readily separated from the ions, giving rise to background noise in the mass spectrum.

Accordingly, a method for separating some of the ions in the gas from each other and from condensed particles in the electrospray is needed to simplify the mass spectra and also to reduce noise.

An efficient method for the separation of ions in a gas utilizes mobility analysis of ions and particles in the gas. Such analysis is based upon the differences in velocity at which different ions drift through the gas, in response to an applied electric field. One such method is based upon the time-of-flight of the ions/particles drifting between two points in the gas. If an analyzer is set only to be responsive to particles arriving within a preset time window, ion/particle selectivity can be achieved. Time-of-flight analysis has been successfully coupled with mass spectrometers to enable a determination of the mass of mobility-selected ions. However, in the time-of-flight analysis approach, ions are separated from each other in dependence upon a time of arrival at a detector. This complicates their introduction into most types of mass spectrometers which utilize atmospheric pressure sources. Such mass spectrometers tend to rely on the use of a steady, rather than a pulsed, ion input. Further, the approach of filtering out of the mass spectrometer inlet all ions from a time of flight mobility spectrum, except those within a small mobility range, causes a substantial loss in ion signal.

An alternative approach which avoids the low duty cycle that results from the use of the time-of-flight method, is based on mobility separation in space rather than in time. Instruments capable of performing a steady mobility selection of an ion stream are widely used in aerosol research, where they are commonly referred to as differential mobility analyzers (DMAs). Aerosol DMAs have traditionally been designed to isolate charged objects with relatively small mobilities. They exhibit rather poor resolution and very high losses for molecular ions of greatest analytical interest.

In a DMA, an electric field is established between two plane parallel metal plate electrodes (or two coaxial cylindrical electrodes) by a potential applied therebetween. Ions or particles are injected through a slit in a first electrode. As these charged entities drift in the electric field towards a second electrode, they are deflected in a direction parallel to the plate electrodes, by a flow of clean, ion-free gas which moves parallel to and between the surfaces of the plates. As a result, the position of the ions' impact on the second plate electrode, in relation to the gas stream direction, is an inverse measure of their electrical mobility. A further slit may be made in the second electrode, through which the charged species can be sampled. By alteration of the voltage, selected subsets of the ionic species can be caused to exit through the slit.

The response of DMAs is substantially influenced by Brownian motion which spreads particles of a given mobility around their mean trajectory. As a result, an aerosol sample through an exit slit contains a relatively wide range of ion/particles of varying mobilities (especially in the case of ultra-fine particles). Consequently, most existing aerosol DMAs do not function as monodisperse particle generators, nor do they measure mobilities of particles in the nanometer range with adequate resolution.

A further problem of aerosol DMAs relates to large losses of ions through the sampling lines which lead from an ion source to the analyzing section and then from the analyzing section to the instrument exit. Thus, most electrospray/mass-spectrometry devices sample ions into their vacuum systems at initial concentrations comparable to the very large ones prevailing in the electrospray source (or from an alternative ion source). However, the sampling process, in all available DMAs, reduces this concentration by more than the two orders of magnitude that are typically lost in coupling a time of flight mobility analyzer to a mass spectrometer.

Accordingly, it is an object of this invention to provide an apparatus and method for analysis of an ion stream in a gas, which apparatus and method exhibit a better transmission efficiency than time-of-flight instruments.

It is another object of this invention to provide an apparatus and method for analysis of an ion stream in a gas which enables exclusion of all but a narrow band of ions which exhibit a determined ion mobility.

It is another object of this invention to provide an apparatus and method for analysis of an ion stream in a gas which provides both precise ion selectivity, while providing a continuous stream of selected ions for analysis.

For complex mass spectra involving several large and multiply charged species, it is another object of this invention to provide a procedure to group together the peaks which correspond to same species present in different charge states. This grouping is equivalent to the identification of each of the species giving rise to the mass spectrum, which are otherwise difficult to resolve by mass spectrometry alone.

SUMMARY OF THE INVENTION

An analytical apparatus provides for the separation and analysis of a subset of ions from an ion stream. The apparatus includes an ion supply, such as an electrospray, which provides a population of variously charged ions. An analyzing chamber is coupled to the ion supply and includes a first wall with an inlet orifice for receiving the flow of variously charged ions, and a second wall opposed to the first wall. A laminar gas flow is established within the analyzing chamber and flows parallel to the first and second walls, along a flow axis. The second wall is provided with an outlet orifice that is displaced by a determined distance along the gas flow axis from the inlet orifice. In a preferred embodiment of this invention the axial distance L between the two orifices is approximately twice the distance w between the first and second walls. A potential difference is applied between the first and second walls which causes the flow of ions, introduced via the inlet orifice, to migrate towards the outlet orifice. The laminar gas flow displaces ion flight trajectories along the flow axis, so that only the ions with a mobility near a specific value Zo reach the second wall close enough to orifice 30 to be sampled through it. The value Zo is controlled by the voltage difference between the walls, to which it is inversely proportional. The outlet orifice is coupled to the inlet of a mass spectrometer to enable analysis of the ions emerging from the outlet orifice. It is preferred that the gas flow in the analyzing chamber exhibit a Reynolds number of at least 2000.

DETAILED DESCRIPTION OF THE INVENTION

Figure 1:
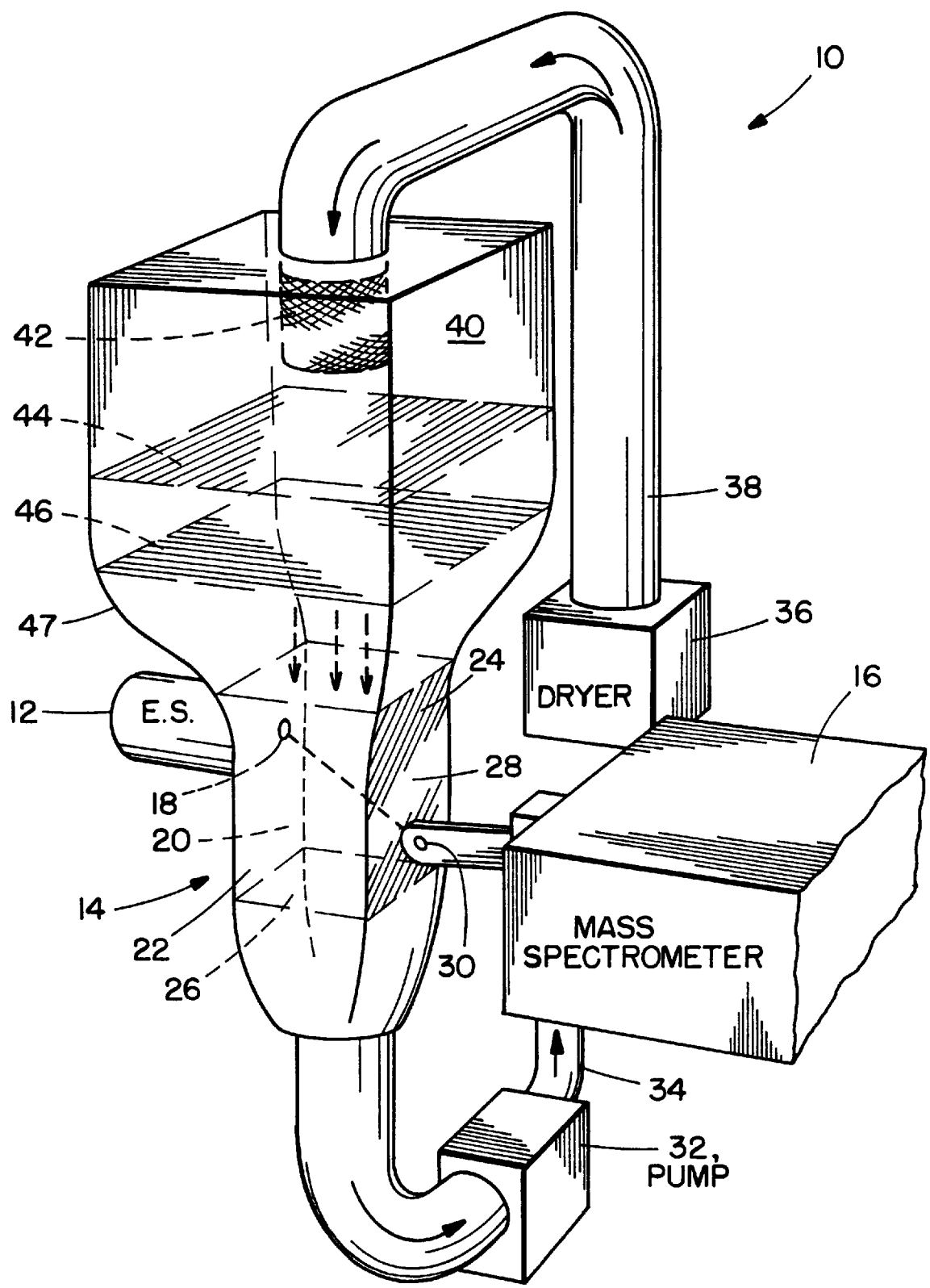
FIG. 1 is a perspective view of an instrument which incorporates the invention.

FIG. 1 is a schematic perspective view of an analytical apparatus 10 incorporating the invention. Apparatus 10 comprises three major components, an electrospray unit 12, a differential mobility analyzer (DMA) 14 and a mass spectrometer 16. Electrospray unit 12 provides a charged population of ions, derived from a sample solution, to an inlet orifice 18 of DMA 14. DMA 14 includes an analyzing chamber 20 which is bounded by side walls 22, 24 and front and rear walls 26, 28, respectively. Side wall 22 includes inlet orifice 18 and side wall 24 incorporates an outlet orifice 30. A power supply (not shown in FIG. 1) applies a potential difference between side walls 22 and 24, so as to establish an electric field therebetween which acts upon ions introduced through inlet orifice 18.

Front and rear walls 26 and 28 of DMA 10 are insulated from sidewalls 22 and 24 and may be held at controlled potentials to further steer and center the beam of ions emanating from inlet orifice 18 towards outlet orifice 30.

A pump 32 provides a gas flow via conduit 34 to a dryer 36 and thence, via conduit 38, to a flow control chamber 40, and a laminarizing flow contraction region 47. Thereafter, the gas passes through analyzing chamber 14 and is exhausted by pump 32.

In flow control chamber 40, an inlet screen 42 causes a diffusion of the inlet gas flow throughout flow control chamber 40. Thereafter, the gas flow experiences a first screen 44 and then a second screen 46. Both screens 44 and 46 are selected to have grid sizes which force the gas flow to achieve a laminar state when the gas enters analyzing chamber 14. For instance, first screen 44 may be provided with a grid size of 40 microns and second screen 46 a grid size of 74 microns. Subsequently, the flow is further laminarized by acceleration through flow contraction region 47 (designed similarly to the inlet of a wind tunnel). The laminarization of the gas flow is greatly aided by the contraction in cross section of the flow stream between flow control chamber 40 and analyzing chamber 20. The acceleration imparted to the flow in this region ensures a greater level of laminarity.

Flow control chamber 40 and analyzing chamber 20 are designed to enable laminar gas flow within analyzing chamber 20 at very high flow rates. More specifically, flow control chamber 40 and analyzing chamber 20 are designed to provide non-turbulent flow at Reynolds numbers of 2000 and higher, with a preferred Reynolds number in the range of $10^4$ or greater. As is known to those skilled in the art, the Reynolds number is a dimensionless number which is equal to the density of a fluid times its velocity times a characteristic length, divided by the fluid's viscosity coefficient. The length in this case is chosen as the distance "w" between plates 22 and 24. The velocity value is the average gas velocity inside analyzing chamber 20.

To prevent turbulent flow which often occurs in the case of high Reynolds numbers, the walls of analyzing chamber 20 and flow contraction region 47 are very smooth and free from discontinuities.

It is preferable to introduce as little gas as possible through the inlet orifice 18, since the resulting gas jet would, if sufficiently intense, tend to favor transition towards turbulent conditions in the main gas flow through analyzing chamber 20. Inlet orifice 18 is drilled in a thin plate, whose thickness is typically half the orifice diameter, such that the electric field may penetrate sufficiently through the orifice. This drives the electrospray ions into analyzing chamber 20, without the need to introduce any gas through inlet orifice 18.

The net flow through inlet orifice 18 may be controlled as follows: Under recirculating conditions for the gas, the flow rate Q (lit/min) into the pump is nearly identical to the flow out of the pump. Thus, the balance $q_b = q_o - q_i$ between the inlet flow rate $q_i$ (lit/min) through inlet orifice 18 and the outlet flow rate $q_o$ of gas passing through outlet orifice 30 must be added into the sheath air flow at a point sufficiently downstream from the outlet orifice 30. Otherwise $q_i$ would not be zero or small as preferred, but would rather be equal to $q_o$. Inlet flow $q_i$ may be brought to an optimal value near zero by causing $q_b$ to be close to the outlet flow $q_o$.

It is also preferable to use a short axial distance L between inlet and outlet orifices 18 and 20, such that less time is available for the high Reynolds number flow to undergo transition to turbulent conditions within the analyzing region. In a preferred arrangement, L should be larger than distance w between plates 22 and 24, but not larger than 2 or 3 times w, since greater lengths increase diffusion broadening, as well as favor transition to turbulence.

The Brownian motion which causes a spread of particles as they traverse from inlet orifice 18 to outlet orifice 30 is minimized by the provision of highly laminar gas flow (at a high Reynolds number) through analyzing chamber 20, as well as by use of a short analyzing chamber. These features enable substantial improvement in ion discrimination at outlet orifice 30. Further detailed description regarding DMA 14 will be provided during the discussion of FIG. 2.

The ions exiting from outlet orifice 30 are fed into the initial stages of a mass spectrometer 16 for mass analysis. Because only a small fraction of the ions in the mixture (those having a mobility very near a preset value Zo) are passed into the mass spectrometer, its ability to resolve individual mass peaks even in relatively complex mixtures is greatly increased.

For a given ion mixture, the output from the coupled DMA-Mass Spectrometry system comes in the form of a detector intensity I which varies when either the DMA voltage (uniquely related to the mobility Z) or the charge over mass (q/m) scale of the mass spectrometer are modified. An instrument incorporating the invention thus yields a response signal I(Z, q/m) which depends on independent variables Z and q/m. ordinarily, this signal intensity is constituted by a series of well resolved peaks rising sharply at a finite number of points in the (Z, q/m) plane.

Figure 3:
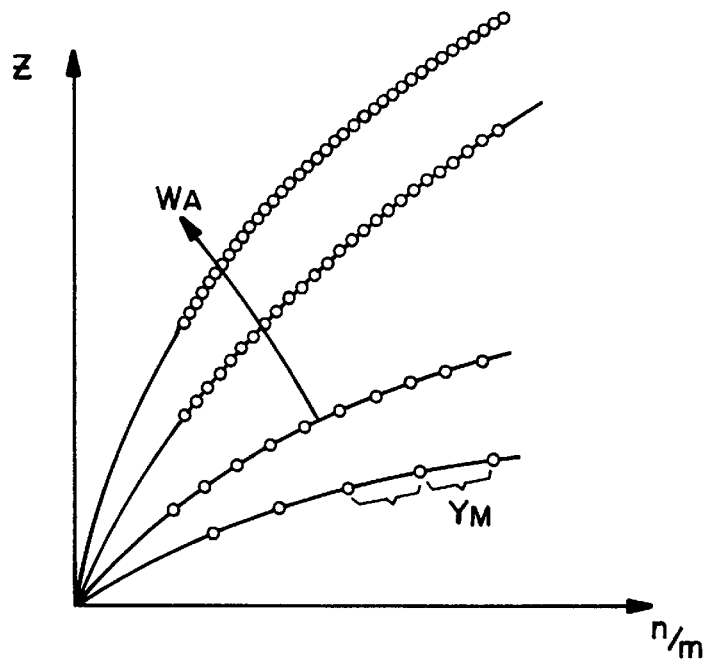
FIG. 3 is a schematic plot of mobility versus charge-over-mass ratio for four different multiply charged macromolecules, each of the four curves corresponding to one macromolecule. Each point in each curve is associated with a different charge state of the corresponding macromolecule.

The essential information contained in one such spectrum can be conveyed by simply plotting each one of these (Z, q/m) pairs in a cartesian coordinate system. Based on data from experiments published by D. E. Clemmer, R. R. Hudgins and M. F. Jarrold, in the Journal of the American Chemical Society, Vol. 117, page 1041 (1995), such a plot may be constructed for the case of cytochrome c, where each point corresponds to a different charge state of the protein, including from 7 up to 20 charges. Each one of the four curves in FIG. 3 is a schematic rendition of such data for four different proteins, some smaller, some larger than cytochrome c. The various points are sufficiently close to each other for their continuous sequence to be recognized, so that they may be joined into a single curve. The points in each of these curves are related to each other in a sequence which allows a confirmation to be made whether one mass peak does or does not belong to one curve.

To a first approximation, the horizontal distance between consecutive points in one curve is equal to 1/m for all points in that curve. They are therefore approximately equidistant along the horizontal scale. More precisely, contiguous points of this series should fall in a sequence of the form $q/m=en/(m+np)$, where e is the elementary charge, m the mass of the analyte ion, n the number of elementary charges it carries and p the mass of each of the n cations or anions attached to it. If two macromolecules are present in the electrosprayed solution, the pairs (Z,q/m) at which peaks appear in the signal will order themselves in a Cartesian plane along two different curves, each of which can be identified with only one species. In cases when two such curves cross or are close enough for ambiguity to arise as to which of the two series a particular peak belongs, the doubt is resolved by the criterion that the horizontal distance in q/m space between contiguous points of this series should fall in a sequence of the form $q/m=en/(m+np)$. Similarly, in a mixture containing several macromolecules, each of which appears in a multiplicity of charge states, the cartesian plot will allow an ordering of each ionic peak within one well defined curve, and each curve will correspond to one of the species in the mixture. This simplifies, considerably, the process of species identification, the main problem of concern to the analytical chemist.

Figure 2:
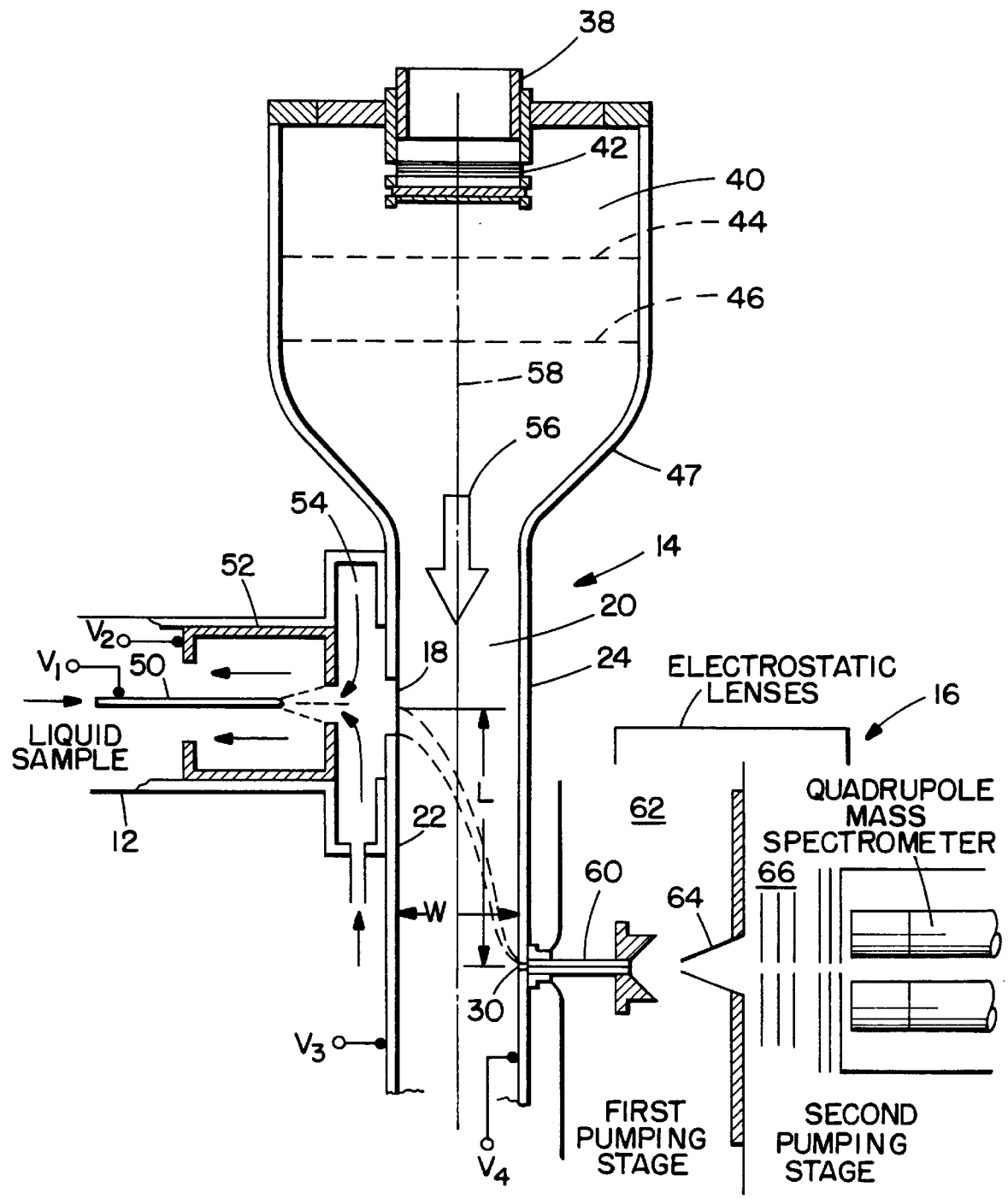
FIG. 2 is a schematic sectional view of the instrument of FIG. 1.

Turning to FIG. 2, further details of analytical apparatus 10 will be described. Elements in FIGS. 1 and 2 that are identical are numbered identically.

Electrospray unit 12 includes a capillary 50 through which a liquid is introduced that carries the solute species to be ionized. The end of capillary 50 is positioned within a cylindrical electrode 52. Voltages V1 and V2 are applied between the liquid meniscus at the end of capillary 50 and cylindrical electrode 52 and establish a high potential which leads to the emission of a charged aerosol spray from capillary 50. A heated drying gas, flowing countercurrent to the aerosol, is introduced via housing 54. The operation of electrospray unit 12 is known and further details regarding it can be found in U.S. Pat. No. 5,523,566 to Fuerstenau et al. and in U.S. patent application Ser. No. 08/808,127 to Gomez et al., assigned to the same Assignee as this Application, the disclosures of which are incorporated herein by reference.

The ionized aerosol from electrospray unit 12 is directed towards inlet orifice 18 and into analyzing chamber 20. When no gas flow is ingested through the inlet orifice 18, this flow of ions is assisted by controlling the voltage difference V2–V3. Voltages V3 and V4 are applied between walls 22 and 24 of analyzing chamber 20 and provide a driving force on the ionic species entering through inlet orifice 18. The laminar flow of gas (indicated by arrow 56) is directed parallel to flow axis 58 and exhibits a high velocity through analyzing chamber 20. The gas flow drives downwards the ionized species introduced through inlet orifice 18.

Gas flow 56, combined with voltages V3 and V4 cause ions that lie within a narrow range of mobilities to be drawn towards and through outlet orifice 30 in wall 24. The mobility of the ions which are extracted from analyzing chamber 20 through outlet orifice 30 may be controlled by varying the values of V3 and V4. Outlet orifice 30 forms the atmospheric pressure inlet to mass spectrometer 16, which inlet comprises a capillary structure 60 that lies within a first pumping stage 62 of the spectrometer. The ionic species emitted from capillary 16 pass through a skimmer 64 and into a second pumping stage 66 of mass spectrometer 16. Within mass spectrometer 16, the ionic species with a preselected mass over charge (m/q) are transmitted and provide output currents in accordance therewith.

In a typical configuration, the distance w between plates 22 and 24 is 1 cm, and the axial distance L between orifices 18 and 30 is 2 cm. A typical flow rate at $Re=10^4$ is 100 lit/min. A typical voltage difference of several KV is applied between plates 22 and 24. Typical dimensions of the orifices are 0.2 mm. The inlet orifice is drilled in a thin plate with a typical thickness of 0.1 mm. The outlet orifice needs not be drilled in a thin plate, since a net gas flow is sampled into the mass spectrometer, carrying the ions with it.

Figure 4:
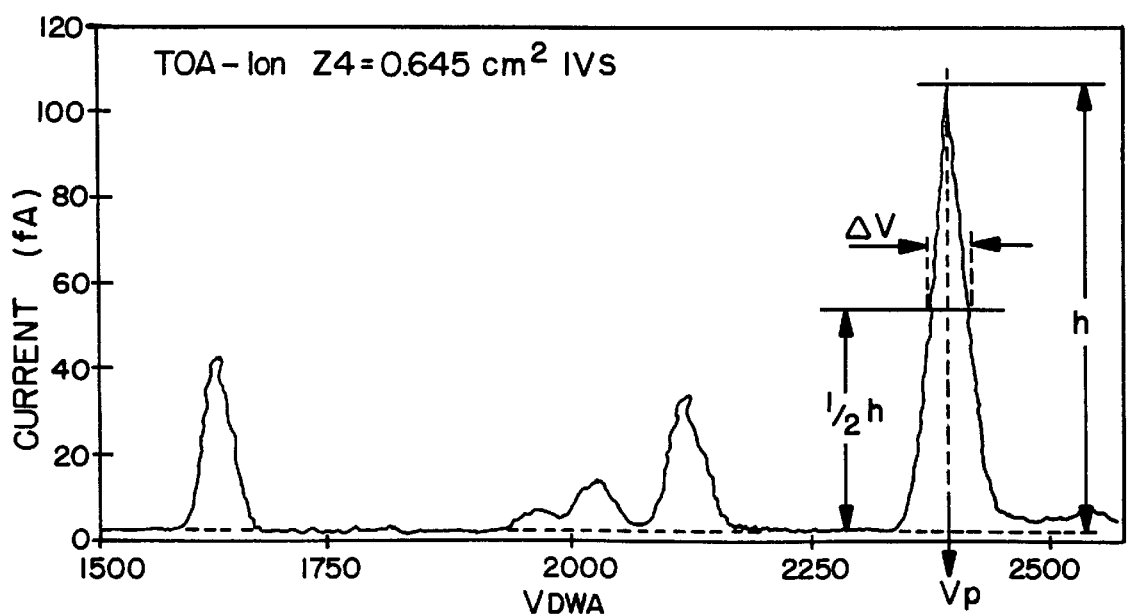
FIG. 4 is a plot illustrating the resolution that is available from a DMA of preferred dimensions, run laminarly at very high Reynolds number.

FIG. 4 illustrates the resolution available from a short, high Reynolds number, DMA configured similarly to that described above. The data are from the Senior Graduation Thesis presented to Fachhochschule Offenburg (Germany; May 1997) by Mr. Thilo Eichler, entitled "A Differential Mobility Analyzer for ions and nanoparticles; Laminar flow at high Reynolds numbers". That device uses slits rather than orifices as inlets and outlets to the analyzing chamber. It has an annular rather than a square cross section, and has high losses in the lines connecting the electrospray to the inlet slit. However, its length is also approximately twice the distance between the electrodes, and it also operates laminarly at Reynolds numbers exceeding $10^4$. The laminarization process used in the instrument is also similar to that described for the instrument shown in FIGS. 1 and 2, with comparable screen configurations and laminarization region following the screens. These features are the ones which determine resolution, and, therefore, FIG. 4 illustrates well the resolution characteristic of the present invention.

A solution of tetrabutyl ammonium salt was electrosprayed and sampled-into the analyzing chamber of this DMA. The current of ions or particles drawn through the sampling slit was measured in an electrometer and is represented as the vertical coordinate. The horizontal coordinate is the voltage difference between the two DMA electrodes. FIG. 4 shows several peaks. The dominant one appearing near 2400 volts is well separated from other ion peaks, as well as from the continuum peak of residue particles, lying to its right (not shown). The resolution R is defined as the inverse of the relative full width at half height: $R=V_p/dV$, where both quantities are indicated in the Figure. The Reynolds number is 21,000. The resolution in this case is larger than 50.

It should be understood that the foregoing description is only illustrative of the invention. Various alternatives and modifications can be devised by those skilled in the art without departing from the invention. Although the sketches show a DMA of square cross section, a circular cross section is easier to construct and would work as well or better. This circular body would then be made out of an insulating material, while four conducting symmetrically placed axial strips inserted in this insulating wall would play the role of the four walls in FIGS. 1 and 2. Also the term ion used throughout refers not only to molecular ions, but also to charged clusters and in general to any charged particle. Accordingly, the present invention is intended to embrace all such alternatives, modifications and variances which fall within the scope of the appended claims.

I claim:

1. A method for separating ions in an ion mixture, comprising:

a) providing a flow of variously charged ions, including a selected species of charged ions to be analyzed, to an analyzing chamber having a gas flow axis, an inlet orifice for receiving said flow of variously charged ions and an outlet orifice that is displaced by a determined distance along said gas flow axis from said inlet orifice;

b) applying a potential between said inlet orifice and outlet orifice to cause said flow of variously charged ions introduced via said inlet orifice to move in a trajectory away from said inlet orifice;

c) providing a laminar gas flow within said analyzing chamber and coaxial with said flow axis, to displace flight trajectories of said variously charged ions along said flow axis, said determined distance of said outlet orifice set to position said outlet orifice to intercept a trajectory of said selected species of charged ions, said laminar gas flow exhibiting a Reynolds Number of at least 2000.

2. The method as recited in claim 1, further including the step of:

d) analyzing ions emerging from said outlet orifice; and wherein steps a)–c) provide a substantially continuous ion flow for analysis in step d).

3. The method as recited in claim 2, wherein step d) performs a mass analysis of said selected species of charged species.

* * * * *